(12) United States Patent
Guskey et al.

(10) Patent No.: US 6,555,099 B2
(45) Date of Patent: Apr. 29, 2003

(54) SINGLE-PHASE ANTIPERSPIRANT COMPOSITIONS CONTAINING SOLUBILIZED ANTIPERSPIRANT ACTIVE AND VOLATILE SILICONE

(75) Inventors: Gerald John Guskey, Montgomery, OH (US); John Paul Luebbe, Lawrenceburg, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/735,165

(22) Filed: Dec. 12, 2000

(65) Prior Publication Data

US 2002/0110532 A1 Aug. 15, 2002

(51) Int. Cl.$^7$ ............. A61K 7/32; A61K 7/34; A61K 7/38; A61K 7/00
(52) U.S. Cl. ............. 424/65; 424/66; 424/68; 424/400; 424/401
(58) Field of Search ............. 424/65, 66, 68, 424/400, 401

(56) References Cited

U.S. PATENT DOCUMENTS

| | | | |
|---|---|---|---|
| 4,822,602 A | 4/1989 | Sabatelli | |
| 5,429,816 A | 7/1995 | Hofrichter et al. | |
| 5,654,362 A | 8/1997 | Schulz, Jr. et al. | |
| 5,919,437 A | 7/1999 | Lee et al. | |
| 5,922,308 A | 7/1999 | Brewster et al. | |
| 5,942,215 A | 8/1999 | Edwards et al. | |
| 5,958,386 A | 9/1999 | Sawin et al. | |
| 5,968,489 A | 10/1999 | Swaile et al. | |
| 5,989,531 A | * 11/1999 | Schamper et al. | ............ 424/65 |
| 6,013,248 A | 1/2000 | Luebbe et al. | |
| 6,060,546 A | 5/2000 | Powell et al. | |
| 6,083,493 A | 7/2000 | Swaile | |
| 6,096,298 A | 8/2000 | Swaile | |
| 6,103,250 A | 8/2000 | Brieva et al. | |

FOREIGN PATENT DOCUMENTS

| | | |
|---|---|---|
| EP | 0404532 | 12/1990 |
| WO | WO 9323008 | 11/1993 |
| WO | WO 99/51192 | 10/1999 |

* cited by examiner

Primary Examiner—Shelley A. Dodson
(74) Attorney, Agent, or Firm—Jack L. Oney

(57) ABSTRACT

Disclosed are single-phase antiperspirant compositions and corresponding methods of application, wherein the compositions are single-phase systems that comprise a solubilized antiperspirant active, a volatile silicone and selected coupling materials that are substantially free of Si—OH and Si—H functional groups and that have a solubility parameter of from about 7 to about 12, wherein the sum total solubility parameter of the essential components in the composition is m about 9 to about 13. These compositions provide improved low residue performance, enhanced stability, improved efficacy, and/or improved cosmetics.

28 Claims, No Drawings

SINGLE-PHASE ANTIPERSPIRANT COMPOSITIONS CONTAINING SOLUBILIZED ANTIPERSPIRANT ACTIVE AND VOLATILE SILICONE

FIELD OF INVENTION

The present invention relates to single-phase antiperspirant compositions, which contain solubilized antiperspirant active, volatile silicone and selected coupling agents. These compositions are especially useful in providing low-residue performance in combination with improved cosmetics.

BACKGROUND OF THE INVENTION

Clear or translucent antiperspirant compositions have become increasingly popular among consumers over the past several years. These products are especially popular in that they leave little or no visible residue during and after application to the underarm. These clear or translucent products are most typically formulated as solid sticks or soft gels and contain antiperspirant active that is solubilized in a polar solvent (e.g., water, propylene glycol, ethanol) and suspended in a suitable gellant.

These clear or translucent antiperspirant compositions containing solubilized antiperspirant active, however, tend to deliver poor skin cosmetics and relatively low antiperspirant efficacy. Although these compositions also tend to leave little or no visible residue during and after application, the clear or translucent layer remaining on the skin after application is often sticky or wet-feeling, and to many people is unacceptably irritating to the skin. In addition to poor skin cosmetics, these compositions typically provide less antiperspirant efficacy than other antiperspirant product forms such as anhydrous antiperspirant solids and semi-solids containing solid or undissolved antiperspirant active.

Attempts have been made to reformulate these clear or translucent antiperspirant products containing solubilized antiperspirant active to control skin irritation and improve antiperspirant efficacy and skin cosmetics, wherein the reformulated products contain skin friendly materials such as silicone oils, especially volatile silicone oils such as cyclopentasiloxane. For example, U.S. Pat. No. 6,083,493 (Swaile) and U.S. Pat. No. 5,968,489 (Swaile et al) disclose clear or translucent antiperspirant compositions including single phase systems or solutions, that contain antiperspirant active solubilized in either 1,2-hexandiol or isopropyl glycerol ether, and then coupled with a volatile silicone oil using a dimethiconol coupling agent. These coupled single-phase systems or solutions disclosed by Swaile have a clear or translucent appearance and provide dry application cosmetics, minimal or no skin irritation, and improved antiperspirant efficacy.

It has now been found, however, that dimethiconol-coupled antiperspirant active solutions such as those disclosed by Swaile should be processed at low or ambient temperatures or under similar other conditions to help minimize the undesirable reaction of the dimethiconol coupling agent in solution. It has also been found that these solutions can even be reactive under ambient conditions, whether anhydrous or aqueous, when packaged and stored over prolonged periods of time. It is now believed that the Si—OH functional group on the dimethiconol is responsible for this undesirable reactivity with solubilized antiperspirant active solutions.

It has also been found that these and other clear or translucent antiperspirant compositions containing silicone oils coupled with a solubilized antiperspirant active can be processed at higher temperatures or similar other conditions, and formulated with improved chemical stability after formulation, by selecting a coupling agent that is substantially free of Si—H and Si—OH functional groups and that has a solubility parameter of from about 7 to about 12, wherein the sum of the solubility parameter of the essential components is also from about 9 to about 13.

It has also been found that a clear or translucent antiperspirant composition can be formulated as a single phase system or solution, wherein the system comprises solubilized antiperspirant active, solvent for the antiperspirant active, volatile silicone liquid, and a coupling agent that is substantially free of Si—H and Si—OH functional groups and has a solubility parameter of from about 7 to about 12, and wherein the sum of the solubility parameters of the essential components is from about 9 to about 13. These compositions provide good skin cosmetics (i.e., dry, smooth, non-sticky application), minimal or no skin irritation, minimal or no visible residue during and after application, and improved product stability during high temperature processing and during prolonged storage or shipping.

SUMMARY OF THE INVENTION

The present invention is directed to antiperspirant compositions that are single-phase systems comprising a solubilized antiperspirant active, a volatile silicone and selected coupling materials. These antiperspirant compositions may also comprise a structurant, provided that the composition remains a single phase system. The invention is also directed to a method of controlling malodor and perspiration through the application of the antiperspirant compositions of the present invention.

The compositions and corresponding methods of the present invention provide improved low residue performance, product stability, antiperspirant efficacy, skin feel performance and/or aesthetics.

DETAILED DESCRIPTION

The antiperspirant compositions of the present invention are single-phase systems that comprise solubilized antiperspirant active, solvent for the antiperspirant active, volatile silicone and selected coupling materials. Each of these essential elements is described in detail hereinafter.

The term "single-phase system", as used herein, refers to the antiperspirant compositions of the present invention, wherein all of these compositions are in the form of a solution or microemulsion. In this context, the term "microemulsion" is an art-recognized term that refers to systems other than solutions that behave thermodynamically as a single-phase, i.e., single-phase systems have a single melting temperature, a single refractive index, a single viscosity, and do not readily phase separate.

The term "ambient conditions" as used herein, unless otherwise specified, refers to surrounding conditions at about one atmosphere of pressure (1 atm), at about 50% relative humidity, and at about 25° C. All values, amounts and measurements described herein are obtained under ambient conditions unless otherwise specified.

The term "volatile" as used herein, unless otherwise specified, refers to those materials that are liquid under ambient conditions and which have a measurable vapor pressure at 25° C. These materials typically have a vapor pressure greater than about 0.01mmHg, more typically from about 0.02 mmHg to about 2mmHg, and an average boiling point typically less than about 250° C., more typically less than about 235° C.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The antiperspirant compositions of the present invention can comprise, consist of, or consist essentially of the essential elements and limitations of the invention described herein, as well as any of the additional or optional ingredients, components, or limitations described herein.

Solubilized Antiperspirant Active

The antiperspirant compositions of the present invention comprise an antiperspirant active suitable for topical application to the skin. The antiperspirant active can be any known or otherwise effective antiperspirant active, provided that the antiperspirant active is solubilized in the composition. The concentration of solubilized antiperspirant active in the composition should be sufficient to provide the desired perspiration wetness and odor control, which will typically range from about 0.1% to about 26%, preferably from about 0.5% to about 20%, more preferably from about 6% to about 20%, by weight of the composition. All such weight percentages are calculated on an anhydrous metal salt basis exclusive of water and any complexing agents such as glycine, glycine salts, or other complexing agents.

Preferred antiperspirant actives for use in the compositions of the present invention include astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the antiperspirant compositions include those which conform to the formula:

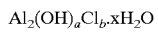

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Processes for preparing aluminum salts are described in U.S. Pat. No. 3,887,692 (Gilman, issued Jun. 3, 1975); U.S. Pat. No. 3,904,741 (Jones et. al., issued Sep. 9, 1975) and U.S. Pat. No. 4,359,456 (Gosling et al., issued Nov. 16, 1982), which descriptions are incorporated herein by reference.

Preferred zirconium salts for use in the antiperspirant compositions include those which conform to the formula:

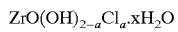

$$ZrO(OH)_{2-a}Cl_a \cdot xH_2O$$

wherein a is any number having a value of from about 0 to about 2; x is from about 1 to about 7; and wherein a and x may both have non-integer values. Particularly preferred zirconium salts are those complexes which additionally contain aluminum and glycine, commonly known as ZAG complexes. These ZAG complexes contain aluminum chlorohydroxide and zirconyl hydroxy chloride conforming to the above described formulas. Such ZAG complexes are described in U.S. Pat. No. 3,679,068 (Luedders et al., issued Feb. 12, 1974) and U.S. Pat. No. 4,120,948 (Shelton, issued Oct. 17, 1978), which descriptions are incorporated herein by reference.

Solvent For Solubilizing Antiperspirant Active

The antiperspirant compositions of the present invention comprise a solvent for solubilizing the antiperspirant active. The solvent can be any solvent known or otherwise effective in solubilizing or helping to maintain solubilization of the antiperspirant actives described herein, and which is otherwise suitable for topical application to the skin. The solvent can therefore be used to solubilize the antiperspirant active during formulation, or may be added to the composition separate from the solubilized antiperspirant active component with the effect of maintaining or further solubilizing the antiperspirant active in the finished product.

The antiperspirant compositions of the present invention comprise solvent for solubilizing the active, wherein the solvent concentration ranges from about 0.1% to about 75%, preferably from about 10% to about 50%, even more preferably from about 15% to about 30%, by weight of the composition. The concentration of the selected solvent will vary depending upon the particular formulation selected, e.g., active concentration selected.

The antiperspirant compositions of the present invention may be aqueous or anhydrous, and therefore the solvent for the antiperspirant active may be aqueous or anhydrous. Both the antiperspirant composition and the solvent are preferably anhydrous. For aqueous embodiments, the antiperspirant compositions may comprise from about 5% to about 75%, preferably from about 10% to about 60%, more preferably from about 15% to about 50%, by weight of water. For anhydrous embodiments, the antiperspirant compositions comprise less than about 5%, preferably less than about 2%, more preferably zero percent, by weight of free or added water.

Suitable solvents for solubilizing the antiperspirant active include water, short chain monohydric alcohols (e.g., C1–C10) such as ethanol, and polyols capable of solubilizing or helping to solubilize the antiperspirant active in the composition. The polyols for use in the antiperspirant composition of the present invention preferably have 2 or more hydroxyl groups with 2 of the hydroxyl groups attached to the α and β carbons of the polyol. The polyols preferably have from about 3 to about 8 carbon atoms, and preferably have either 2 or 3 hydroxyl groups in total.

The polyol solvents for use in the antiperspirant compositions of the present invention are preferably formulated into the composition so that the resulting mole ratio of the polyols to the combination of zirconium and aluminum ions, when such a combination is present in the composition, is at least about 2.0, preferably at least about 2.5, more preferably at least about 3.0. The concentration of antiperspirant active solubilized by the polyols is dependent upon this mole ratio of the 1,2-diols to antiperspirant metal ions (e.g., zirconium and aluminum). Solutions with a mole ratio of polyols to antiperspirant metal ions of less than about 2.0 are unstable and will easily precipitate during the manufacturing process or during storage, so that the maximum concentration of active that should be used to make a stable solution is dependent upon the molecular weight of the polyol solvent, the number of 1,2-diol functional groups per molecule, and the aluminum to zirconium ratio (when present in the composition) making up the active.

The polyol solvents for use in the antiperspirant compositions of the present invention preferably have a ClogP value of less than about 2.0, more preferably from about −4.0 to about 2.0, even more preferably from about −4.0 to about 1.0, even more preferably from about −2.0 to about 1.0, most preferably from about −1.0 to about 0.5. The ClogP values (calculated logP) can be calculated for each polyol by the Pamona Med Chem/Daylight "CLOGP" program, Version 4.42, available from Biobyte Corporation, Claremont, Calif. Other suitable methods for determining ClogP values include the fragment approach described by Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990), which description is incorporated herein by reference. Still other suitable methods are described or provided by Daylight Information Systems, Mission Viejo, Calif., Daylight V4.61, Algorithm: V3.05, Database: V16. General information pertaining to ClogP values and methodologies are described in Chemical Reviews, 93(4),1993, 1281–1306, which description is also incorporated herein by reference.

Non-limiting examples of suitable polyol solvents for use herein include any polyol material that is liquid under ambient conditions, or which is otherwise in liquid form within the selected composition, and has the requisite number and arrangement of hydroxyl groups and has the requisite ClogP value as defined herein. Generally, the preferred polyols for selection and use in the composition of the present invention include alkyl diols, glycerol ethers and other polyol liquids, which correspond to the formula:

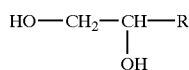

wherein the more preferred polyols have the requisite ClogP and hydroxyl group arrangement as described herein, and wherein R is an alkyl, hydrogen, methyl, hydroxyethyl, ether, ester, amine, amide, alkoxylate, siloxane, functionalized silicone, fluorinated or perfluoroether material, or combination thereof. The R group can be substituted or unsubstituted, branched or straight or cyclic, saturated or unsaturated. The R group is preferably. an alkyl group having from 1 to 6 carbon atoms. Non-limiting examples of suitable substituents on the R group include hydroxyl groups, amines, amides, esters, ethers, alkoxylate groups (e.g., ethoxylates, propoxylates, etc.), siloxanes, functionalized silicones, fluorinated or perfluoroether materials, and combinations thereof.

Examples of suitable alkyl diols for use as antiperspirant solvents herein, and their corresponding ClogP values, for use in the antiperspirant composition include 1,2-propanediol (−0.92), glycerin (−1.76), sorbitol (−2.20), 1,2-butanediol (−0.53), 1,2-pentanediol (0.0), 4-methyl-1,2-pentanediol (0.397), 2-methyl-1,2-pentanediol (0.399), 3,3-methyl-1,2-butanediol (0.267), methyl-1,2-hexanediol (0.50), ethylene glycol (−1.3), and combinations thereof.

Suitable glycerol ethers for use as antiperspirant solvents herein, and their respective ClogP values include glycerol isopropyl ether (−0.51), glycerol propyl ether (−0.73), glycerol ethyl ether (−1.04), glycerol methyl ether (−1.57), glycerol butyl ether (0.01), glycerol isopentyl ether (0.41), diglycerol isopropyl ether (−1.49), diglycerol isobutyl ether (−0.96), diglycerol (−2.95), triglycerol (−3.71), triglycerol isopropyl ether (−2.25), and combinations thereof.

Other suitable polyol liquids, for use as antiperspirant solvents herein, and their respective ClogP values include acetic acid glycerol ester (−1.30), propanoic acid glycerol ester (−0.77), butanoic acid glycerol ester (−0.24), 3-methyl butanoic acid glycerol ester (0.16), 3-trimethylsily-1,2-propane diol (0.56) and combinations thereof. Still other suitable polyols include 1,2,6-hexanetriol (−0.3) and 1,2,4-butanetriol (−1.3).

Preferred polyols for use as antiperspirant solvents herein are 1,2-hexanediol, glycerin and 1,2-propanediol, more preferably a combination of two or more of the following solvents: 1,2-hexanediol, glycerin, 1,2-propanediol, ethanol, and water, most preferably an anhydrous combination excluding added water.

Volatile Silicone Liquid

The antiperspirant compositions of the present invention comprise a volatile silicone liquid that is known or otherwise suitable for application to the skin, and which has the requisite volatility as defined herein. The volatile silicone liquid can be linear, branched or cyclic.

The concentration of the volatile silicone liquid in the antiperspirant compositions of the present invention ranges from about 0.1% to about 50%, preferably from about 1% to about 30%, more preferably from about 5% to about 20%, by weight of the composition. The volatile silicone liquid for use in the antiperspirant composition is preferably a cyclic silicone having from about 3 to about 7, more preferably from about 5 to about 6, even more preferably 5, silicon atoms. Most preferred are those volatile silicone liquids which conform to the formula:

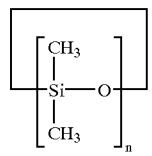

wherein n is from about 3 to about 7; preferably from 5 to 6, most preferably 5. The volatile silicone liquid for use in the antiperspirant composition can also include linear volatile silicones corresponding to the formula

wherein m is from 0 to about 7. The most preferred volatile silicone liquids for use herein include cyclopentasiloxane, cyclohexasiloxane, and combinations thereof. Other volatile silicones include short chain silicones, such as alkyl trimethicones (e.g., caproyl trimethicone), alkyl methicones, alkyl trisiloxanes. Cyclopentasiloxane is most preferred.

Non-limiting examples of suitable volatile silicone liquids for use in the antiperspirant compositions of the present invention are described in U.S. Pat. No. 4,781,917 (Luebbe et al., issued Nov. 1, 1988), and also described by Todd et al., "Volatile Silicone Fluids for Cosmetics", 91, *Cosmetics and Toiletries*, 27–32, (1976), which descriptions are incorporated herein by reference.

Selected Coupling Materials

The antiperspirant compositions of the present invention comprise selected coupling materials in combination with the volatile silicone liquid described hereinbefore. The coupling materials are any material or combination of materials that are selected so as to be substantially free of Si—H or SI—OH functional groups and which form a single-phase mixture, which when added to a mixture of two or more discrete fluid phases, will sufficiently form a miscible, single-phase solution or a microemulsion.

The concentration of the selected coupling materials in the antiperspirant compositions of the present invention ranges from about 0.1% to about 60%, preferably from about 5% to about 40%, even more preferably from about 8% to about 30%, by weight of the composition. Coupling materials act to facilitate the compatibility and solubility between the solubilized antiperspirant active and the volatile silicone or any other incompatible fluid, within the composition.

The solubility parameter of the coupling material is intermediate or between the solubility parameter of the two or more discrete fluid phases used in formulating the composition into a single-phase system. The immiscible fluid phases of which the coupling material is added to during formulation consists of at least one phase being a silicone phase and at least one other phase being the solubilized antiperspirant active phase. The solubility parameter of the coupling material selected for use in the composition must be from about 7 to about 12. The normalized sum of the solubility parameter of the essential components (volatile silicone liquid, selected coupling material, antiperspirant active, solvent for the antiperspirant active), not including the solubility parameter of any optional ingredients, must be from about 9 to about 13, according to the formula:

$$\frac{\sum_{i=1}^{p}[\text{concentration of essential component}]_i \times [\text{solubility parameter of essential component}]_i}{\sum_{i=1}^{p}[\text{concentration of essential component}]_i}$$

Solubility parameters as used to characterize the various volatile silicone liquids, coupling materials, and solubilized antiperspirant actives described herein are determined by methods well known in the chemical arts for establishing the relative polar character of the aforementioned materials. A description of solubility parameters and means for determining them are described by C. D. Vaughan, "Solubility Effects In Product, Package, Penetration and Preservation", 103, *Cosmetics and Toiletries*, 47–69 (October 1988); and C. D. Vaughan, "Using Solubility Parameters in Cosmetics Formulation", 36, *J. Soc. Cosmetic Chemists*, 319–333 (September/October 1988), which descriptions are incorporated herein by reference. It is assumed for purposes of defining the compositions and methods of the present invention, and for purposes of determining the normalized sum of solubility parameters described herein, that the antiperspirant active in the composition has a solubility parameter of 20.

Coupling materials suitable for use in the present invention include any of a variety of materials that are liquid under ambient conditions, having the requisite solubility parameter as described hereinabove and which are characterized as fatty alcohols, fatty esters, fatty ethers, alcohols, esters, ethers or modified silicones. Preferred organic coupling materials include octyldodecanol, $C_9$ alcohol, polypropylene glycol-3 myristyl ether (PPG-3 myristyl ether), propylene glycol monoisostearate, dimethyl isosorbide, diisopropyl adipate, isostearyl benzoate, diisopropyl sebacate, polypropylene glycol-10 cetyl ether, propylene glycol isoceteth-3 acetate, myreth-3 octanoate, polypropylene glycol-15 stearyl ether, octylmethoxycinnnamate, polypropylene glycol-14 butyl ether (such as Fluid AP$^{TM}$ from Witco Chemical), ethanol, isopropyl myristate, octyl salicylate, and $C_{12}$–$C_{15}$ alkyl benzoate (such as Finsolv TN™ from Finetex)), and combinations thereof.

Non-limiting examples of modified silicone liquids for use as coupling solvents in the antiperspirant compositions include those materials that are liquid under ambient conditions and are characterized as methicones, dimethicones, trimethicones and trisiloxanes, preferably those having an oxyalkylene, alkyl, alkylaryl, aryl, hydroxyl, phenyl, and/or styryl moiety attached, non-limiting examples of which include GE CF 1142, GE SF 1023, GE 1205–04–0283, GE 88017, GE SF 1150 (all which are available from General Electric Co.), Masil 756 (available from PPG Specialty Chemicals), Wacker L 066 (available from Wacker Silicones Corp.) and DC 5750 (available from Dow Corning Co.), dimethiconols, silicone polyethers having at least one alkoxylated group. Silicone polyethers having at least one alkoxylated group are most preferred.

Optional Structurant

The antiperspirant compositions of the present invention may comprise a structurant to help provide the composition with the desired viscosity or product hardness, or to otherwise help suspend any dispersed solids or liquids within the composition. Suitable structurants include any material known or otherwise effective in providing suspending or thickening properties to the composition, or which otherwise provide structure to the final product form, and which can be formulated into a single-phase system or solution.

Optional structurants for use in the antiperspirant composition herein include gelling agents, and polymeric or non-polymeric or inorganic thickening or viscosifying agents. Such materials will most typically include organic solids (e.g., fatty alcohols, triglycerides and other esters), silicone solids (e.g., silicone waxes, silicone polyethers) crystalline or other wax-type gellants, inorganic particulates such as clays or silicas, or combinations thereof.

The concentration and type of the structurant selected for use in the antiperspirant composition will vary depending upon factors such as the desired product form, viscosity, and hardness. For structurants suitable for use herein, the concentration of such structurant will most typically range from about 0.1% to about 35%, more typically from about 0.1% to about 20%, by weight of the composition. For antiperspirant compositions containing higher silicone elastomer concentrations, or for low-viscosity or other compositions that derive the desired structure primarily from the silicone elastomer gel material itself, these concentrations will more typically range from about 0.1% to about 10%, even more typically from about 3% to about 9%, by weight of the composition.

Suitable gelling agents for use as structurants in the antiperspirant compositions of the present invention include, but are not limited to, solid materials (i.e., solid within the composition under ambient conditions) such as fatty acid gellants, hydroxy acid gellants, esters and amides of fatty acid gellants, esters and amides of hydroxy fatty acid gellants, cholesterolic materials, dibenzylidene alditols, lanolinolic materials, amides (e.g., fatty amides, polyamides), esters (e.g., fatty esters, triglycerides), fatty alcohols, silicone polyethers, natural gums, cellulosic and functionalized cellulosic materials, waxes (e.g., silicone waxes, organic waxes), polymers, n-acyl amino acid derivatives such as n-acyl amino acid amides, n-acyl amino acid esters or amides prepared from glutamic acid, lysine, glutamine, aspartic acid, amides or esters of citric acid, tricarballylic acid, aconitic acid, sucrose esters, alkyl succindiamides, montmorillonite clays, and colloidal, fumed or gelled silicas. Other suitable amide or ester gelling agents are described in U.S. Pat. No. 5,429,816 (Hofrichter et al., issued Jul. 4, 1995) and U.S. Pat. No. 5,840,287 (Guskey et al., issued Nov. 24, 1998), which descriptions are incorporated herein by reference.

Preferred structurants for use herein include materials selected from a variety of chemical groups. Preferred fatty alcohol structurants include cetyl alcohol, myristyl alcohol, stearyl alcohol, 12-hydroxyl stearyl alcohol, and behenyl alcohol. Preferred wax structurants include beeswax, carnauba, baysberry, candelilla, montan, ozokerite, ceresin, hydrogenated castor oil (castor wax), synthetic waxes, and microcrystalline waxes. Preferred hydroxy fatty acid structurants include 12-hydroxystearic acid, 12-hydroxylauric acid, and 16-hydroxyhexadecanoic acid. Preferred fatty acid structurants include behenic acid, eurcic acid, stearic acid, caprylic acid, lauric acid, and isostearic acid. Preferred ester structurants include esters of 12-hydroxystearic acid (e.g., 12-hydroxystearic acid methyl ester), 12-hydroxystearic acid ethyl ester, 12-hydroxystearic acid stearyl ester, 12-hydroxystearic acid benzyl ester, N,N'-12-hydroxyoctadecanoate ethylene glycol, ethylene glycol distearate, sucrose ester of fatty acids (SEFA) (e.g., SEFA behenate). Preferred amide structurants include amides of 12-hydroxystearic acid such as 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, dodecylsuccindibutylamide, and diisopropyl amide of 12-hydroxystearic acid. Preferred cellulosic structurants include hydroxypropylcellulose, hydroxylmethylcellulose, methylcellulose, ethylcellulose, propylcellulose, and hydroxyethylcellulose. Preferred silicone wax structurants include alkylmethyl siloxanes or silicone waxes (such as hexyl, octyl, lauryl, cetyl, cetearyl, stearyl, behenyl, C20–C24, C24–C28, C30–C45); DC-2501 Cosmetic Wax (Dimethicone Copolyol); DC-2502 Fluid (Cetyl Dimethicone); DC-2503 Wax (Stearyl Dimethicone); DC-580 Wax (Stearoxytrimethylsilane [and] Stearyl Alcohol); DC Q5-0158A wax (stearoxytrimethylsilane); AMS C30 Cosmetic Wax (available from Dow Corning); GE SF-1632 (silicone wax); GE SF-1642 (silicone wax); Abil Wax 9810 (silicone wax or C24–28 methicone); Abil Wax 2434 (Stearoxy Dimethicone); Abil Wax 9800 (Stearyl Dimethicone); and Tegomer H-Si 2111, H-Si 2311, A-Si 2120, A-Si 2320, C-Si 2141, C-Si 2341, E-Si 2130, E-Si 2330, V-Si 2150, V-Si 2550, H-Si 6420, H-Si 6440, H-Si 6460 (Alpha-Omega Dimethicone. Copolymers); Preferred silicone polyethers are DC 190, DC 193, DC 3225C, DC 5225C, BY 11-030 and modifications (available from Dow Corning); GE SF-1188, SF-1188A, SF-1288, SF-1328 (available from General Electric Silicones); Abil EM-90 and EM-97 (available from Goldschmidt). Preferred triglyceride structurants include tristearin, hydrogenated vegetable oil, trihydroxysterin (Thixcin® R, available from Rheox, Inc.), rape seed oil, fish oils, tripalmiten, tribehenin available as Syncrowax® HRC and Syncrowax® HGL-C (Syncrowax® available from Croda, Inc.). Preferred silica structurants include Cab-O-Sil® (available from Cabot Corp.) and other fumed silica materials. Preferred montmorillonite clay structurants include bentonites, hectorites, and colloidal magnesium aluminum silicates.

Optional Liquid Carrier

The antiperspirant compositions of the present invention may further comprise a liquid carrier in addition to the volatile silicone liquid, coupling material and the antiperspirant solvent as described hereinbefore. The liquid carrier can be any liquid material that is compatible with the essential ingredients in the composition, and which is otherwise suitable for topical application to the skin. In this context, the optional liquid carrier is any liquid material added to the antiperspirant composition in addition to and other than the volatile silicones and solvents described hereinbefore.

The optional liquid carrier may be added to the antiperspirant compositions of the present invention for any desired purpose, including as emollients, surfactants, solvents, coupling agents, or any other desired purpose. The liquid carrier may be volatile or non-volatile, polar or non-polar, organic or silicone-containing, fluorinated, and/or water-miscible or immiscible. The concentration of the optional liquid carrier in the antiperspirant compositions of the present invention can range from about 0.1% to about 95%, more typically from about 5% to about 60%, even more typically from about 8% to about 40%, by weight of the composition.

Non-Volatile Silicone Liquid

The optional liquid carrier of the antiperspirant composition of the present invention may comprise a non-volatile silicone liquid. Non-limiting examples of non-volatile silicone liquids for use herein include modified silicone carriers, provided that such carriers are liquid under ambient conditions, are not volatile as defined herein, and have a viscosity of from about 5 centistokes to about 100,000 centistokes, preferably less than about 10,000 centistokes, more preferably from about 10 centistoke to about 1,000 centistokes, and even more preferably from about 10 centistoke to about 100 centistokes. These modified silicone carriers are generally known in the chemical arts, some examples of which are described in *Cosmetics, Science and Technology* 27–104 (M. Balsam and E. Sagarin ed. 1972); U.S. Pat. No. 4,202,879 (Shelton, issued May 13, 1980) and U.S. Pat. No. 5,084,577 (Bolich, issued Jan. 28, 1992), which descriptions are incorporated herein by reference.

The modified silicone liquid carriers suitable for use in the antiperspirant compositions include, but are not limited to, compounds or materials as defined hereinabove and which are generally characterized as follows: silicone polyethers or silicone glycols (such as dimethicone copolyol); silicone alkyl-linked polyethers (such as Goldschmidt Abil EM-90 or Abil EM-97); iloxane surfactants of a pendant/rake/comb configuration, silicone surfactants of a trisiloxane configuration, and silicone surfactants of ABA/alpha-omega block copolymers (such as polyoxyalkylenes, polyoxyethylene or ethoxylated, polyoxypropylene or oxypropylene, polyoxyethylene/polyoxypropylene or ethoxylated/propoxylated); aromatic substituted silicone emollients (such as phenyl, alpha-methyl styryl, styryl, methylphenyl, alkylphenyl); silicone copolymers with other functional groups include: hydrogen, hydroxyl, hydroxyalkyl, polyhydroxy alkyl, alkyl, methyl, amino, trifluoropropyl, vinyl, alkoxy, arylalkyl, aryl, phenyl, styryl, polyethers, esters, carboxylics; nonionic functional siloxane copolymers with terminal groups being silanol or trimethylsiloxy; nonionic functional siloxanes with backbone groups being trisiloxane or methicone linked; nonionic silicone surfactants; tetraethoxysilane; tetramethoxysilane; hexamethoxysilicone; oxymethoxytrisiloxane; silicone emulsifiers; silicone or siloxane resins, alkyl silicone resins, polyoxyalkylene silicone resins; MQ resins, alkoxysiloxanes; alkoxysilanes; methicones; and combinations thereof.

Non-limiting examples of suitable modified silicone carriers for use in antiperspirant compositions herein include the following modified silicones available from Dow Corning: DC-556 Cosmetic Grade Fluid (phenyl trimethicone); DC-704 Diffusion Pump Fluid (Tetramethyl-Tetraphenyl-Trisiloxane); DC-705 Diffusion Pump Fluid; DC-1784 Emulsion; DC-AF Emulsion; DC-1520; DC-593 Fluid (Dimethicone [and] Trimethylsiloxysilicate); DC-3225C or DC-5225C Fluid (Cyclomethicone [and] Dimethicone Copolyol); DC-190 Fluid (Dimethicone Copolyol); DC-193 Fluid (Dimethicone Copolyol); BY-11-030 (Cyclomethicone [and] Dimethicone Copolyol); DC-1732, DC-5732, DC-5750, DC-1401 (Cyclomethicone [and] Dimethiconol); DC-5200, Fluid (Laurylmethicone Copolyol); DC-6603 Polymer Powder; DC-5640 Powder; DC-Q2-5220 (Dimethicone Copolyol); DC Q2-5324 (Dimethicone Copolyol); DC-1-3563 (Dimethiconol); DC-X2-1286 (Dimethiconol); DC-X2-1146A (Cylcomethicone [and] Dimethiconol); DC-8820 Fluid (Amino functionalized); DC-Q2-8220 (Trimethylsilylamodimethicone); DC-7224 (Trimethylsilylamo-dimethicone); DC-X2-1318 Fluid (Cyclomethicone [and] Vinyldimethicone); DC-QF1-3593A fluid (Trimethylsiloxysilicate); and combinations thereof.

Other nonlimiting examples of suitable modified silicone carriers for use in the antiperspirant compositions herein include the following modified silicones available from General Electric: GE SF-1023 (Dimethyl-Diphenyl-Siloxane); GE SF-1066, GE CF-1142 (Methylphenyl Siloxane Fluid); GE SF-1153 (Dimethyl-Diphenyl-Siloxane); GE SF-1265 (Diphenyl-Dimethyl-Siloxane); GE SF-1188 (Dimethicone copolyol); GE SF-1188A (Silicone polyether copolymer); GE SF-1288 (silicone polyether copolymer, dimethyl-methyl 3-hydroxypropyl ethoxylated siloxane); GE SF-1318 (methylester siloxane); GE SF-1328 (silicone surfactant, dimethyl-methyl 3-hydroxypropyl ethoxylated-propoxylated siloxane); GE SF-1550 (methylphenyl siloxane, hexamethyl-3-phenyl-3-[[trimethylsilyl]oxy] trisiloxane); and combinations thereof.

Other nonlimiting examples of suitable modified silicone carriers for use in the antiperspirant compositions herein include the following: Masil 756 from PPG Specialty Chemicals (Tetrabutoxypropyl Trisiloxane); bis-phenylhexamethicone (available as Silbione Oils 70633 V30 from Rhone-Poulenc); Silbione Oils 70646 (dimethicone copolyols from Rhone-Poulenc); Unisil SF-R (dimethiconol from UPI); Silicate Cluster from Olin (Tris[tributoxysiloxy] methylsilane); silicone copolymer F-754 (dimethicone copoly from SWS Silicones); and combinations thereof.

The non-volatile silicone fluid may also comprise a dimethicone, preferably in combination with a modified silicone carrier as described hereinbefore. These non-volatile silicone carriers are preferably linear silicones which include, but are not limited to, those which conform the formula:

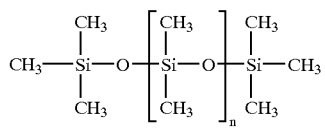

wherein n is greater than or equal to 8. Preferably, non-volatile dimethicones have a viscosity as measured at 25° C. of at least about 3 centistokes to about 1,000 centistokes, more preferably from about 3 centistokes to about 1,000 centistokes, even more preferably from about 3 centistokes to about 100 centistokes, most preferably from about 10 centistokes to about 50 centistokes. Examples of non-volatile, linear silicones suitable for use in the antiperspirant compositions include, but are not limited to, Dow Corning 200 Fluid, Rhodorsil Oils 70047 (available from Rhone-Poulenc), Masil SF Fluid (available from PPG Specialty Chemicals), Dow Corning 225 Fluid, SF-96, SF-1214, SF-1236 and CF-1251 Silicone Fluids (available from G.E. Silicones), DMF A-6 and DM Fluid line (available from Shin Etsu), Viscasil and gums such as GE SE Fluid (available from G.E. Silicones), Siloxane F-221 and Silicone Fluid SWS-101 (available from SWS Silicones), and combinations thereof.

Volatile, Nonpolar Hydrocarbon Liquid

The optional liquid carrier may also comprise a volatile, nonpolar hydrocarbon liquid, including volatile branched chain hydrocarbons having from about 4 to about 30 carbon atoms, preferably from about 4 to about 20 carbon atoms, more preferably from about 6 to about 20 carbon atoms, non-limiting examples of which include the isoparaffins available from Exxon Chemical Company (Baytown, Tex. U.S.A.), as Isopar M (C13–C14 Isoparaffin), Isopar C (C7–C8 Isoparaffin), Isopar E (C8–C9 Isoparaffin), Isopar G (C10–C11 Isoparaffin), Isopar L (C11–C13 Isoparaffin), Isopar H (C11–C12 Isoparaffin), and combinations thereof. Other non-limiting examples of suitable branched chain hydrocarbons include Permethyl 99A (isododecane), Permethyl 102A (isoeicosane), Permethyl 101A (isohexadecane), and combinations thereof. The Permethyl series are available from Presperse, Inc. (South Plainfield, N.J., U.S.A.). Other non-limiting examples of suitable branched chain hydrocarbons include petroleum distillates such as those available from Phillips Chemical as Soltrol 130, Soltrol 170, and those available from Shell as Shell Sol 70, –71, and –2033.

Nonlimiting examples of other suitable nonpolar, volatile hydrocarbon liquids include dodecane, octane, decane, hydrogenated polyisobutanes and combinations thereof, and the Norpar ™ series of paraffins available from Exxon Chemical Company such as Norpar 12, –13, and –15. Yet another example includes C11–C15 alkanes/cycloalkanes, such as those available from Exxon as Exxsol™ D80.

Non-Volatile, Nonpolar Hydrocarbon Liquid

The optional liquid carrier in the antiperspirant compositions of the present invention may comprise a non-volatile, nonpolar liquid, non-limiting examples of which include mineral oil, petrolatum, and certain other branched-chain, non-volatile hydrocarbons. Mineral oils useful in the antiperspirant compositions of the present invention include petroleum derivatives which are complex mixtures of paraffinic and naphthenic (cyclic) hydrocarbons. These include both "light" and "heavy" mineral oils, which are differentiated on the basis of the average molecular weight of the hydrocarbons included. The mineral oils useful herein have the following properties: viscosity of from about 5 centistokes to about 70 centistokes at 40° C.; density between about 0.82 and about 0.89 g/cm$^3$ at 25° C.; flash point between about 138° C. and about 216° C.

The branched chain hydrocarbons useful as carrier liquids herein are typically highly-branched, non-volatile aliphatic liquids containing an average of from about 16 to about 68, preferably from about 20 to about 40, carbon atoms.

Fluorochemical Liquid

The optional carrier liquid may also comprise fluorochemicals such as fluorotelomers and perfluoropolyethers, some examples of which are described in "Using Fluorinated Compounds in Topical Preparations", 111, *Cosmetics and Toiletries*, 47–62, (October 1996) which description is incorporated herein by reference. More specific examples of suitable fluorochemicals include, but are not limited to, perfluoroethers, perfluoropolymethyl isopropyl ethers, perfluoropolypropylethers, acrylamide fluorinated telomer, fluorinated amide surfactants, perfluorinated thiol surfactants. Other more specific examples include, but are not limited to, the polyperfluoroisopropyl ethers available from Dupont Performance Chemicals under the trade name Fluortress® PFPE oils, and the fluorosurfactants from Dupont Performance Chemicals under the trade name Zonyl® Fluorosurfactants. Still other suitable fluorochemicals for use herein include hydrofluoroethers such as Extractive 7100 (available from 3M), FPE and RfoMe fluids (available from Daikin, Japan), and the Flutec™ series (available from Cosmetic Innovations and Technologies, Nord, France).

Deodorant Active

The antiperspirant compositions of the present invention may comprise deodorant actives. These deodorant actives may be used in addition to or in place of some or all of the antiperspirant active material, and include any known or otherwise safe and effective deodorant active suitable for topical application to the skin.

Deodorant actives suitable for use in the composition of the present invention include any topical material that is known for or otherwise effective in preventing or eliminating malodor associated with perspiration, preferably antimicrobial deodorant actives.

Antimicrobial deodorant actives suitable for use herein include cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether, 3,4,4'-trichlorocarbanilide, diaminoalkyl amides such as L-lysine hexadecyl amide, heavy metal salts of citrate, salicylate, and piroctose, especially zinc salts and acids thereof, heavy metal salts of pyrithione, especially zinc pyrithione, zinc phenolsulfate, farnesol, octoxyglycerin and combinations thereof. Preferred antimicrobial agents are 2,4,4'-trichloro-2'-hydroxy diphenyl ether (triclosan) and/or 3,4,4'-trichlorocarbanilide (triclocarban).

The concentration of the deodorant active in the composition ranges from about 0.01% to about 10%, preferably from about 0.1% to about 5%, more preferably from about 0.1% to about 1%, by weight of the composition.

Other Optional Ingredients

The antiperspirant compositions of the present invention may further comprise other optional ingredients to modify the physical, chemical, cosmetic or aesthetic characteristics of the compositions or to serve as additional "active" components when deposited on the skin. The compositions may also further comprise optional inert ingredients. Many such optional ingredients are known for use in deodorants, antiperspirants or other personal care compositions, and may also be used in the antiperspirant compositions herein, provided that such optional materials are compatible with the essential materials described herein, or do not otherwise unduly impair product performance.

Non-limiting examples of other optional ingredients suitable for use in the antiperspirant compositions herein include fragrances, pH buffering agents, soothing agents, dyes and pigments, medicaments, propellants, baking soda and related materials, preservatives, and combinations thereof.

Method of Manufacture

The compositions of the present invention may be made by any of the methods known in the art for formulating antiperspirant compositions, or which are otherwise effective in formulating such compositions. As will be apparent to those skilled in the art, the particular method will be dependent upon factors such as the specific types and amounts of the components employed, as well as the final product form and product characteristics. Specific non-limiting examples of such methods are described hereinafter.

Product Form

The antiperspirant compositions of the present invention can be formulated in any liquid, solid, semi-solid, or form, provided that the selected form is a single-phase system and contains all of the essential elements as defined herein. These compositions can be formulated as opaque, translucent or clear formulations, preferably as translucent or clear formulations. The compositions are preferably formulated as liquids, semi-solids or gels, more preferably liquids, and even more preferably as clear or translucent liquids, including sprays (e.g., pump and aerosol).

The antiperspirant compositions of the present invention are preferably packaged into any container or applicator suitable for use in applying the composition to the axilla or other suitable area of the skin. For the preferred liquid embodiments of the present invention, the antiperspirant composition is preferably packaged into a porous dome applicator. A non-limiting example of a porous dome applicator suitable for use herein is disclosed in U.S. Pat. No. 4,936,700 (Morris, issued Jun. 26, 1990), which description is incorporated herein by reference.

Method For Use

The antiperspirant compositions of the present invention are formulated in final form to be topically applied to the axilla or other area skin to control malodor and perspiration. These methods comprise applying to the axilla or other area of the skin a safe and effective amount of the antiperspirant composition of the present invention. In this context, the term "safe and effective amount" means an amount of the antiperspirant composition topically applied to the skin that is effective in inhibiting or minimizing odor and perspiration at the site of application while also being safe for topical use at a reasonable risk/benefit ratio. In this context, a safe and effective amount typically ranges from about 0.1 gram per axilla or other area of the skin to about 2.0 gram per axilla or other area of the skin, preferably from about 0.5 gram to about 1.0 gram per axilla or other area of the skin. The compositions are preferably applied to the axilla one or more times daily, preferably once daily.

EXAMPLES

The following Examples 1–16 illustrate specific embodiments of the antiperspirant compositions and methods of the present invention, but are not intended to be limiting thereof.

Other modifications can be undertaken by the skilled artisan without departing from the spirit and scope of this invention.

Each of the exemplified compositions is applied topically to the axilla in an amount effective to inhibit or prevent perspiration, typically an amount which ranges from about 0.1 gram to about 2.0 grams per axilla. The applied compositions are effective in inhibiting perspiration and malodor from the applied areas, have good skin feel characteristics during and after application, and leave little or no visible residue on the skin. The applied compositions are mild to the skin and cause little or no skin irritation. All of the exemplified compositions contain a coupling agent having a solubility parameter of from about 9 to about 12, wherein all of the essential ingredients in each exemplified composition has a normalized sum of the solubility parameter of the essential components (volatile silicone liquid, selected coupling material, antiperspirant active, solvent for the antiperspirant active), not including the solubility parameter of any optional ingredients, of from about 9 to about 13. All exemplified amounts are weight-weight percentages based upon the total weight of the composition, unless otherwise specified.

Each of the exemplified compositions (1–16) can be prepared by first solubilizing the antiperspirant active in the selected solvent (or obtaining antiperspirant active in solubilized form), placing the solubilized antiperspirant active in an appropriate vessel. An appropriate coupling material is added to the solubilized active and mixed thoroughly at 500 revolutions per minute (rpm) for 5 minutes, using a twin turbine blade (IKA Labortechnik type, available from Janke & Kunzel, GmbH & Co., Germany), until a uniform mixture is formed. The volatile silicone liquid is added to the combination and then mixed together until a dispersed and homogenous composition is formed. All other optional ingredients (except any fragrances, dyes, deodorant actives, or other heat sensitive materials) are then added to the composition and mixed thoroughly at 500 rpm for 30 minutes. If an optional structurant is added, at this point the composition is heated with all components (except any fragrances, dyes, deodorant actives, or other heat sensitive materials) until the structurant has been melted. The melting point of most suitable structurants will typically range from about 40° C. to about 150° C. The final ingredients are then added (such as any fragrances, dyes, deodorant actives, or other heat sensitive materials) and subsequently cooled to just about above the solidification temperature of the composition, typically to about 40° C. to about 70° C. The resultant composition is dispensed into an appropriate package. Unless otherwise specified, all process steps described herein are performed under ambient conditions.

As an example, the composition described in Example 1 is formulated by first preparing a 30% antiperspirant active solution using a 1,2-hexanediol solvent to solubilize the active. Preparation of solubilized active is disclosed in U.S. Pat. No. 5,968,489 (Swaile et al, issued Oct. 19, 1999), which disclosure is incorporated herein by reference. The antiperspirant active solution is then placed in an appropriate vessel, and 20 parts of additional 1,2-hexanediol solvent is added to make a 25% active/1,2-hexanediol solution. The diluted active solution is mixed thoroughly (500 rpm, 30 minutes), using a twin turbine blade, until a clear solution is formed. In a separate vessel, 60 parts of this diluted active solution and 15 parts of octyldodecanol are combined and mixed thoroughly together (500 rpm, 30 minutes). Then, 24 parts cyclopentasiloxane are added to this combination, and mixed thoroughly (500 rpm, 30 minutes). Fragrance at 1 part is then added to this composition and mixed thoroughly (500 rpm, 5 minutes). In this particular example, all process steps are performed under ambient conditions, unless otherwise specified. The resultant composition is dispensed into an appropriate package.

The compositions described in Examples 1–6 are packaged in a porous dome application. The compositions are clear to translucent in appearance and are applied to the axilla by the methods described above.

TABLE I

Liquid Antiperspirant Compositions.

| Ingredient | Ex. 1 | Ex. 2 | Ex. 3 | Ex. 4 | Ex. 5 | Ex. 6 |
|---|---|---|---|---|---|---|
| 1,2-hexanediol | 45 | 20 | 30 | 45 | — | 40 |
| Glycerin | — | — | 30 | — | 45 | 40 |
| Aluminum/zirconium trichlorohydrex gly (% by weight powdered active, solubilized in solvent) | 15 | — | 15 | — | 15 | — |
| Aluminum/zirconium tetrachlorohydrex gly (% by weight powdered active, solubilized in solvent) | — | 10 | — | 15 | — | 10 |
| Cyclopentasiloxane (D5) | 24 | 0.1 | 5 | 24 | 14 | 6 |
| Octyldodecanol | 15 | — | — | 15 | — | — |
| PEG-8 | — | 69.9 | — | — | — | — |
| Silicone Polyether | — | — | 19.5 | — | 25 | 4 |
| Fragrance | 1. | — | 0.5 | 1. | 1 | — |

TABLE II

Gel/Semi-solid Antiperspirant Compositions.

| Ingredient | Ex. 7 | Ex. 8 | Ex. 9 | Ex. 10 | Ex. 11 | Ex. 12 |
|---|---|---|---|---|---|---|
| 1,2-hexanediol | 45 | 45 | 40 | 30 | 29.7 | — |
| Glycerin | — | — | — | 25 | 20 | 25 |
| Aluminum/zirconium trichlorohydrex gly (% by weight powdered active, solubilized in solvent) | 5 | — | 10 | — | — | — |
| Aluminum/zirconium tetrachlorohydrex gly (% by weight powdered active, solubilized in solvent) | — | 11 | — | 15 | — | 10 |
| Triclosan | — | — | — | — | 0.3 | — |
| Cyclopentasiloxane (D5) | 19 | 19.5 | 10 | 14 | 19.5 | 20 |
| Diisopropyl sebacate | 20 | — | — | — | — | 20 |
| Octyldodecanol | 4 | 24 | — | — | — | 5 |
| PPG-3-myristyl ether | — | — | 39 | — | — | — |
| PEG-8 | — | — | — | — | — | 20 |
| Silicone polyether | 6 | — | — | 15 | 30 | — |
| Hydroxy propyl cellulose | — | — | 1 | — | — | — |
| Fragrance | 1. | 0.5 | — | 1. | 0.5 | — |

TABLE III

Solid Antiperspirant Compositions.

| Ingredient | Ex. 13 | Ex. 14 | Ex. 15 | Ex. 16 |
|---|---|---|---|---|
| 1,2-hexanediol | 35 | 30 | — | — |
| Glycerin | — | — | 20 | 20 |
| Aluminum/zirconium trichlorohydrex gly (% by weight powdered active, solubilized in solvent) | 15 | — | 12 | — |
| Aluminum/zirconium tetrachlorohydrex gly (% by weight powdered active, solubilized in solvent) | — | 15 | — | 12 |
| Silicone polyether | 20 | 20 | 20 | 20 |
| Cyclopentasiloxane (D5) | 19 | 19.5 | 20 | 19 |
| PEG-8 | — | 5 | 25 | 18 |
| Tribehenin | 10 | — | — | — |
| Stearyl alcohol | — | 10 | — | — |
| Dibenzylidene sorbitol | — | — | 2.5 | — |
| Hydroxypropyl cellulose | — | — | 0.5 | — |
| N,N'-12-hydroxyoctadecanoate ethylene glycol | — | — | — | 10 |
| Fragrance | 1 | 0.5 | — | 1 |

What is claimed is:
1. An anhydrous antiperspirant composition comprising:
(a) a solubilized antiperspirant active;
(b) a solvent for solubilizing the antiperspirant active;

(c) a volatile silicone liquid; and (d) a coupling material that is substantially free of SI—H and SI—OH groups and has a solubility parameter of from about 7 to about 12, wherein the composition is an anhydrous single-phase system and has a normalized sum of solubility parameters for components (a), (b), (c) and (d) of from about 9 to about 13.

2. An antiperspirant composition according to claim 1, wherein the composition comprises from about 0.1% to about 26% by weight of the antiperspirant active, from about 0.1% to about 75% by weight of the solvent for solubilizing the antiperspirant active, from about 0.1% to about 50% by weight of the volatile silicone, and from about 0.1% to about 60%, by weight of the coupling material.

3. An antiperspirant composition according to claim 2, wherein the composition comprises from about 6% to about 20% by weight of the antiperspirant active.

4. An antiperspirant composition according to claim 2, wherein the composition comprises from about 15% to about 30% by weight of the solvent.

5. An antiperspirant composition according to claim 2, wherein the composition comprises from about 5% to about 20% by weight of a volatile silicone liquid selected from the group consisting of cyclopentasiloxane, cyclohexasiloxane and combinations thereof.

6. An antiperspirant composition according to claim 2, wherein the composition comprises from about 8% to about 30% by weight of the coupling material.

7. An antiperspirant composition according to claim 2, wherein the composition further comprises from about 5% to about 60% by weight of a liquid carrier other than and in addition to the coupling material, the volatile silicone liquid, and the solvent for solubilizing the antiperspirant active.

8. An antiperspirant composition according to claim 2, wherein the composition comprises from about 0.1% to about 20% by weight of a structurant.

9. An antiperspirant composition according to claim 3, wherein the solubilized antiperspirant active is selected from the group consisting of aluminum salts, zirconium salts, and combinations thereof.

10. An antiperspirant composition according to claim 9, wherein the solubilized antiperspirant active is an aluminum-zirconium complex.

11. An antiperspirant composition according to claim 4, wherein the solvent has a ClogP of less than about 2.

12. An antiperspirant composition according to claim 6, wherein the coupling material is a silicone polyether.

13. An antiperspirant composition according to claim 1, wherein the composition is a liquid.

14. An antiperspirant composition according to claim 1, wherein the composition is a semi-solid.

15. An antiperspirant composition according to claim 1, wherein the composition is a solid.

16. An antiperspirant composition according to claim 1, wherein the composition comprises from about 6% to about 26% by weight of solubilized alurninum-zirconium complex, from about 30% to about 45% by weight of 1,2-hexanediol, from about 1% to about 20% by weight of cyclopentasiloxane, and from about 8% to about 40% by weight of a silicone polyether.

17. An antiperspirant composition according to claim 1, wherein the composition comprises from about 6% to about 26% by weight of solubilized aluminum-zirconium complex, from about 30% to about 45% by weight of glycerin, from about 1% to about 20% by weight of cyclopentasiloxane, and from about 8% to about 40% by weight of a silicone polyether.

18. An antiperspirant composition according to claim 1, wherein the composition comprises from about 6% to about 26% by weight of solubilized aluminum-zirconium complex, from about 30% to about 45% by weight of water, from about 1% to about 20% by weight of cyclopentasiloxane, and from about 8% to about 40% by weight of a silicone polyether.

19. A deodorant composition comprising:

a) an antimicrobial deodorant active;

b) a volatile silicone; and c) a coupling material;

wherein the composition is a single-phase system.

20. A deodorant composition according to claim 19, further comprising a structurant.

21. A deodorant composition according to claim 19, wherein the composition comprises from about 0.01% to about 10% by weight of the deodorant active, from about 5% to about 20% by weight of the volatile silicone, and from about 8% to about 40% by weight of the coupling material.

22. An aqueous antiperspirant composition comprising:

(a) a solubilized antiperspirant active;

(b) a solvent for solubilizing the antiperspirant active;

(c) a volatile silicone liquid; and (d) a coupling material that is substantially free of SI—H and SI—OH groups and has a solubility parameter of from about 7 to about 12, wherein the composition is an aqueous single-phase system having a normalized sum of solubility parameters for components (a), (b), (c) and (d) of from about 9 to about 13.

23. An antiperspirant composition according to comprises from about 0.1% to about 60% by weight of a liquid carrier other than and in addition to the coupling solvent and the solvent for the antiperspirant active.

24. An antiperspirant composition according to claim 23, wherein the composition further comprises from about 0.1% to about 20% by weight of a structurant.

25. An antiperspirant composition according to claim 22, wherein the solubilized antiperspirant active is an aluminum-zirconium complex.

26. A method of controlling malodor and perspiration comprising the topical application of from about 0.1 gram to about 2.0 gram per axilla of the anhydrous antiperspirant composition of claim 1.

27. A method of controlling malodor comprising the topical application of from about 0.1 gram to about 2.0 gram per axilla of the deodorant composition of claim 19.

28. A method of controlling malodor and perspiration comprising the topical application of from about 0.1 gram to about 2.0 gram per axilla of the aqueous antiperspirant composition of claim 22.

* * * * *